United States Patent [19]

Zech

[11] 4,302,438

[45] Nov. 24, 1981

[54] ANTIGEN, ANTISERUM AND IMMUNOASSAY FOR THEOPHYLLINE

[75] Inventor: Karl Zech, Konstanz, Fed. Rep. of Germany

[73] Assignee: Byk Gulden Lomberg Chemische Fabrik GmbH, Konstanz, Fed. Rep. of Germany

[21] Appl. No.: 110,441

[22] Filed: Jan. 8, 1980

[30] Foreign Application Priority Data

Jan. 13, 1979 [DE] Fed. Rep. of Germany ....... 2901218

[51] Int. Cl.$^3$ .................. G01N 33/58; G01N 33/60; C07G 7/00; C07D 473/00
[52] U.S. Cl. .................................. 424/1; 23/230 B; 260/112 B; 424/12; 424/88; 544/271; 435/7
[58] Field of Search ................. 424/1, 12, 88; 23/230 B; 260/112 B; 435/7; 544/271

[56] References Cited

U.S. PATENT DOCUMENTS 4,156,081  5/1979  Singh et al. .................. 544/271

OTHER PUBLICATIONS

Koup et al., Chem. Abstracts, vol. 89, 1978, abstract #99518x.
Nishikawa et al., Chem. Abstracts, vol. 90, 1979, Abstract #51014y.

*Primary Examiner*—Christine M. Nucker
*Attorney, Agent, or Firm*—Berman, Aisenberg & Platt

[57] ABSTRACT

By injecting a host animal with a member of a particular group of antigens [a theophylline-(7)-alkanecarboxylic acid covalently bonded to an immunogenic carrier (IGC) via the carboxyl group], antibodies, advantageously employed in determining small amounts of theophylline in biological liquids by immunoassay methods, are obtained.

40 Claims, No Drawings

ANTIGEN, ANTISERUM AND IMMUNOASSAY FOR THEOPHYLLINE

THE TECHNICAL FIELD

Radioimmunoassay (RIA), enzymeimmunoassay (EIA) and fluorescentimmunoassay (FIA) methods are used for the determination of theophylline in biological liquids, such as whole blood and haemolytic blood. Particularly suitable antibodies for these methods are obtained by injecting a suitable host animal with one of a select group of novel antigens.

BACKGROUND

Theophylline (1,3-dimethylxanthine) is a medicament which is used widely, particularly for the treatment of the bronchitic syndrome and also for the treatment of high blood pressure and of renal edema. It is also used for treating temporary asphyxia in premature babies.

A process for obtaining a theophylline antiserum is described in *Research Communications in Chemical Pathology and Pharmacology*, 13, 497 (1976), the antiserum being obtained by immunizing rabbits by a conjugate of theophylline-(8)-butyric acid and bovine serum albumin (BSA). A process for obtaining antibodies specific for caffeine is known from *J. Pharmacol, Exp. Ther.*, 199, 579 (1976), the process being based on immunization of rabbits by theophylline-(7)-caproic acid coupled to BSA.

STATEMENT OF INVENTION

Because of the relative narrowness of the therapeutic range for theophylline and because serum levels vary greatly from patient to patient, a sensitive and inexpensive analytical method is needed for individual determinations and for monitoring theophylline serum levels. Such analytical process should be as free as possible from influence by normal metabolities of theophylline and by other xanthine derivatives, such as caffeine, occuring in serum.

Immunoassay methods employing antibodies produced in animal hosts with one of a select group of antigens have been found to satisfy these prerequisites. These antibodies impart a particularly high specificity and superior sensitivity to the immunoassay methods employing them.

The invention has a number of distinct aspects which combine together in producing a single ultimate and unified result—immunoassay procedures made possible by antigens in the structure of which theophylline is substituted in the 7-position. The antigens, which comprise the first aspect of the invention, are compounds of formula I:

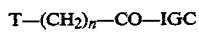
(I)

wherein
  T is a theophylline-(7) radical,
  n is 2, 3 or 4 and
  IGC is an immunogenic carrier.

Other aspects of the invention include (but are not limited to) the following:

(2) Use of an antigen of formula (I) to produce antiserum;
(3) Antiserum so produced;
(4) An immunoassay reagent composition wherein antiserum is in admixture with a labelled compound, e.g. a theophylline determination agent wherein the antiserum is (3) and the labelled compound, such as labelled theophylline, is one which forms a complex with antibodies of the antiserum.
(5) Antibodies of the antiserum;
(6) A theophylline/antibody complex formed in an immunoassay process; and
(7) Use of the complex in theophylline determination.

DETAILS

The antigen has a structure in which a haptene of formula II:

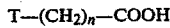
(II)

wherein
  T is theophylline-(7), and
  n is an integer from 2 to 4, inclusive,
is covalently bonded via the carboxyl group to IGC. Preferred antigens are those wherein n is 3 or 4, particularly those wherein n is 3.

Immunogenic carriers are known, as is a suitable method for covalently bonding them, via the carboxyl group (—COOH), to the haptene. Compounds of formula II are conventionally prepared.

To prepare the theophylline-(7)-alkanecarboxylic acids, theophylline is converted into a metal salt, preferably an alkali metal salt. This is appropriately effected in an inert, anhydrous solvent, e.g. dimethylformamide, dimethylacetamide or acetonitrile, by reaction with a metal hydride, preferably an alkali-metal hydride, such as sodium hydride or lithium hydride. The theophylline salt is alkylated with a functional derivative of an n-alkanecarboxylic acid, preferably an ester thereof, which carries a nucleofugic leaving group in the ω-position. A nucleofugic leaving group is understood, in particular, as a chlorine, bromine or iodine atom, preferably a bromine atom, or a sulfonyloxy group, such as p-toluenesulfonyloxy, benzenesulfonyloxy or methanesulfonyloxy, preferably toluenesulfonyloxy. The resulting theophylline-(7)-alkanecarboxylic acid derivative is then conventionally converted into the free acid or a salt thereof. Saponification of a theophylline-(7)-alkane-carboxylic acid ester is effected, for example, by means of an alkali-metal hydroxide, in particular potassium hydroxide. Theophylline-(7)-butyric acid is the preferred haptene and is readily prepared in this manner, as are the other contemplated haptenes.

The covalent bonding of the theophylline-(7)-alkanecarboxylic acids of formula II to IGC is effected in a manner which is also known. Various types of proteins and polypeptides which, on injection into host animals, spontaneously cause an immune reaction in the host animal are used as IGC. Preferred examples are mammalian serum proteins, such as human γ-globulin, human serum albumin, hare serum albumin, bovine γ-globulin and bovine serum albumin (BSA). The latter is the particularly preferred IGC in the context of this invention. Those proteins which are foreign to the host animal are peferably, but not necessarily, used. Synthetic polypeptides, such as polymers of lysine, polymers of glutamic acid and the like, either by themselves or in combination, are suitable alternatives to proteins for this purpose.

The covalent bonding of a compound of formula II to IGC is effected, e.g., in a manner customary for producing ester bonds or amide bonds. The use of known peptide-synthesis methods, e.g., is recommended. In one embodiment, for example, a compound of formula II is converted, before coupling to IGC, into an activated form which is isolatable. A suitable activated form which is isolatable is, for example, the N-hydroxysuccinimide ester. The p-nitrophenyl ester is also suitable. In a preferred embodiment, the activated form is prepared by reaction with a carbodiimide or, in particular, with N,N'-carbonyldiimidazole in a suitable solvent, such as dimethylformamide, acetonitrile, tetrahydrofurane, dimethylsulfoxide or hexamethylphosphoramide. A particularly advantageous method of producing covalent coupling of a compound of formula II to IGC is the mixed anhydride process. In this process, a compound of formula II is dissolved in an inert, water-soluble organic solvent, for example a cyclic ether, such as dioxane, and the solution is neutralized with a tri(lower alkyl)amine, such as tri-(n-butyl)amine. A haloformic acid lower-alkyl ester, such as chloroformic acid isobutyl ester, is subsequently added. The resulting solution is then added to a solution of the IGC in water or in a 1:1 mixture, for example, of water and a water-soluble organic solvent (for example a cyclic ether, such as dioxane) at a temperature between 0° and 8° C., the solution of the IGC being rendered alkaline beforehand with the aid of a solution of an alkali-metal hydroxide, such as sodium hydroxide. The coupling reaction is continued for a period lasting between half an hour and half a day. The desired antigen is obtained after dialyzing, acidifying and centrifuging.

As is readily understood, when IGC is a protein, the carboxyl group of the haptene of formula II forms an amide with an amino group of the protein. When IGC has a hydroxy group which reacts with the haptene carboxyl group, an ester is formed.

The antigen is not specifically limited to any one or any group of IGC, nor is any IGC restricted by the selected value of n within the scope of formula I. For each value of n, IGC is thus virtually any immunogenic carrier. At least the specific IGC is not critical to the invention beyond its definition in any claim. Enumerated IGC's are merely illustrative, and that of each provided example is equally exemplary of all other IGC's with which it is optionally replaced to provide corresponding products and results. Similar comments apply to the contemplated variation in the value of n.

Antigens of formula I are useful to induce, in a host animal, the formation of antibodies specific towards theophylline. This is achieved by injecting the host animal with the antigen, preferably with the addition of a customary auxiliary, such as "Freund's complete adjuvant", and including a buffer, preferably a phosphate buffer of pH 7.4. Examples of suitable host animals are mammals, such as rabbits, horses, goats, guinea pigs, rats, cattle or sheep. Rabbits are preferred in the present invention. The formation of antibodies is intensified by repeated injection, whereupon antisera with a high titre of antibodies are obtained. The antisera containing the antibodies are conventionally obtained from the blood of the host animal.

The antibodies thus obtained are distinguished by their superior sensitivity. Surprisingly, they also permit problem-free determination of theophylline directly from whole or complete blood, as well as from haemolytic blood. The fact that, after a sample has been taken, complete blood can be diluted to an extent such that no degradation of the theophylline is to be feared is also considered advantageous; using the process according to the invention, precise determination of theophylline level in diluted samples is possible even after storage at room temperature for several days. After being taken, the blood samples are diluted and sent (without particular precautionary measures with regard to temperature, such as cooling) to a place where the theophylline determination (according to the invention) is carried out.

The antigens of formula I are critical precursors of the antisera which provide essential reagents and antibodies for contemplated immunoassay theophylline determinations. The reagents comprise an admixture of antiserum (produced by an antigen of formula I) with labelled theophylline.

The antibodies (in the antiserum) per se and their use in theophylline immunoassay determinations are fundamental aspects of the invention.

In order to apply an immunoassay to determine the amount of theophylline in a sample of body fluid, e.g. whole blood, the sample is mixed with a known or fixed amount of labelled theophylline and an antibody (which has been produced by injecting one of the previously-described antigens into a host animal) which reacts with theophylline to form a complex, the degree of bonding of the labelled theophylline is measured, and the amount of theophylline present in the sample is determined from this measurement by comparison with a standard curve obtained by adding known amounts of theophylline to a defined mixture of labelled theophylline and the antibody. This method, known as immunoassay, is conventional.

Special embodiments of immunoassay methods include radioimmunoassay (RIA), those wherein the labelled theophylline is labelled with a radioactive element, e.g. $^{125}$iodine; enzymeimmunoassay (EIA), those wherein the labelled theophylline is labelled with an enzyme, e.g. glucose-6-phosphate-dehydrogenase; and fluorescentimmunoassay (FIA), those wherein the labelled theophylline is fluorescently labelled, e.g., with 7-methoxy-4-methylcoumarin or fluorescein.

The labelled theophylline, e.g. that which is radioactively labelled, is not limited to theophylline itself; it is optionally any of a wide range of theophylline derivatives which also form a complex with the antibodies. The derivative is, e.g., a compound of formula II, a corresponding theophylline-(8) compound or an amide of either with, e.g., histamine, tyramine, tyrosine, tyrosine methyl ester or tyrosine ethyl ester. The provided (radioactively-, enzyme- or fluorescent-) labelled theophylline competes with unlabelled theophylline in a body-fluid sample for theophylline-specific-binding sites of the antibodies of the antiserum to form a precipitating complex with the antibodies which can be separated from uncomplexed theophylline. When there is only a very small amount of theophylline in the body fluid, the precipitate (complex) contains a relatively large amount of labelled and detectable theophylline, and vice versa. The sole purpose of the labelled theophylline is for the determination of the amount of theophylline in the sample; it has no special use in the production of antisera.

The reagent is characterized by its content of labelled theophylline and antiserum or, more specifically, antibodies of the previously-described antisera. In a preferred embodiment the reagent also contains, as is customary in corresponding commercial reagents, all the auxiliary agents necessary for carrying out an immunoassay determination, such as a standard solution, a buffer solution, a precipitating agent and an agglutinating agent, in ready-to-use form.

The immunoassay method according to the invention is distinguished, above all, by its high specificity, i.e., in addition to its superior sensitivity. Cross-reactions with potentially-present purine substances (in addition to theophylline in the liquids to be investigated) are encountered to a lesser extent than with antibodies produced by different antigens. Thus, for example, the crossreaction with caffeine is only 2.5 percent. In addition, the reagents of the immunoassay method according to the invention have a very long storage life; portions not used in one series of measurements are availalbe and viable for use in later determinations of theophylline.

Radioactively-labelled theophylline is theophylline or a theophylline derivative which is labelled with a radioisotope, such as tritium ($^3$H), carbon 14 ($^{14}$C), iodine 125 ($^{125}$I) or iodine 131 ($^{131}$I). The preferred $^3$H-labelled theophylline is 8-$^3$H-theophylline, which is prepared in a known manner by reducing 8-bromotheophylline by means of tritium ($^3$H$_2$) on palladium-on-charcoal. In the context of this invention, theophylline compounds labelled with iodine$^{125}$ or iodine$^{131}$ are, in particular, active iodination products of theophylline-(7)-alkanecarboxylic acid N-(2-imidazol-4-ylethyl)amides, N-[2-(4-hydroxyphenyl)ethyl]amides and N-[1-carboxy- or -methoxy- or -ethoxycarbonyl-2-(4-hydroxyphenyl)ethyl]amides. The corresponding theophylline-(8)-butyric acid amides are similarly useful. Theophylline-(7)-butyric acid N-(2-imidazol-4-ylethyl)amide labelled with $^{125}$iodine is preferred, and theophylline-(7)-butyric acid N-[2-(4-hydroxyphenyl)ethyl]amide labelled with $^{125}$iodine is particularly preferred.

The preparation of these theophylline-(7)-alkanecarboxylic acid amides from compounds of formula II by reaction with tyramine, histamine and tyrosine (or methyl or ethyl esters thereof) is effected by processes which are customary to experts in the preparation of carboxylic acid amides, and such as are described, for example, in Houben-Weyl, "Methoden der organischen Chemie" (Methods of Organic Chemistry), Volume XI/2, pages 3–25 (1958) and Volume XV, pages 1–396 (1974).

Enzyme-labelled theophylline is theophylline or a theophylline derivative which is coupled to an enzyme, for example katalase, peroxidase, β-glucoronidase, β-D-glucosidase, β-D-galactosidase, urease, malate dehydrogenase, alkaline phosphatase, glucose oxidase and galatose oxidase. Enzymes which catalyst transformations of substrates, where colored products are generated or disappear, are particularly appropriate since they make possible the determination of the enzyme in a simple manner by a colorimetric measurement. The coupling of theophylline derivatives to glucose-6-phosphate dehydrogenase is preferred. In this case the determination of the amount of the conjugate between the theophylline derivative and the enzyme is effected by reaction with nicotinamide-adenine dinucleotide (NAD). The amount of NADH generated is determined spectrophotometrically by measurement of the absorption at 340 nm. As theophylline derivatives coupled to glucose-6-phosphate dehydrogenase theophylline-(7- or -8)-[N-(2-aminoethyl)]butyramide and (7- or -8)-(4-amino-n-butyl)theophylline are preferred. The coupling of theophylline derivatives to enzymes is effected in a manner which is in itself known. Theophylline derivatives (with at least one free amino group which is coupled to a free carboxyl group of the enzyme) are preferably employed. The coupling of the amino group with the carboxyl group is done by reactions known from peptide chemistry. Special examples of such couplings of haptenes with proteins are, for example, described in "Immunology and Immunochemistry", Volume 1. The enzymeimmunologic determination of substances is known to persons skilled in the art, for example, from Sharpe et al., Clin. Chem., 22, 733 to 738 (1976), German Pat. Nos. 21 55 658 and 21 64 768 and German patent specifications (laid open to public inspection) 25 45 980 and 28 34 141.

Fluorescence-labelled theophylline is theophylline or a theophylline derivative which is coupled to a fluorescent substance, for example, the dansyl (5-dimethylamino-1-naphthalenesulfonyl) rest and other substituted naphthalines, o-phthaldialdehyde, pyrrolin-4-one, the dimethoxyanthracenesulfonyl rest, 7-methoxycoumarin, 7-methoxy-4-methylcoumarin and other coumarin derivatives, and fluorescein. As theophylline derivatives which are fluorescene labelled, theophylline-(7- or -8)-butyric acid, its 2-aminoethylamide, and (7- or -8)-(4-amino-n-butyl)theophylline are preferred. As fluorescence labels 7-methoxy-4-methylcoumarin and fluorescein are preferred. The coupling of the theophylline derivative to the fluorescene label is effected in a manner which is in itself known. For example, in Chard et al., Clin. Chem., 25, 973 to 975 (1979), the labelling of a substance with fluorescein by the use of fluorescein isothiocyanate is described. The determination of the fluorescencelabelled theophylline is done in the usual way with a spectrofluorometer.

The new antigens and antibodies of the present invention are used, e.g., with customary additives, buffers, stabilizers and diluents.

The invention is illustrated by the following examples.

EXAMPLE 1

Preparation of theophylline-(7)-butyric acid (a) Theophylline-(7)-butyric acid ethyl ester 4.8 g (0.1 mol) of 50 percent strength sodium hydride are added to 18.0 g (0.1 mol) of theophylline (dissolved in 150 ml of anhydrous dimethylformamide) at room temperature, while stirring. When the evolution of hydrogen has ended, 21.5 g (0.11 mol) of 4-bromobutyric acid ethyl ester are added dropwise, while stirring continuously, and the mixture is then heated to 100° C. for 2 hours. The solution is evaporated in vacuo, and the residue is taken up in methylene chloride. The sodium bromide which has precipitated is filtered off from the resulting solution; the filtrate is extracted twice by shaking with water, dried over anhydrous sodium sulfate and evaporated in vacuo. The resulting crystal mass is recrystallized from isopropanol. 25.2 g of the ester (86.4 percent of the theoretically calculated amount) of melting point 79° to 80° C. are thus obtained.

Replacing the 4-bromobutyric acid ethyl ester with an equivalent of the ethyl ester of either 3-bromopropionic acid or 5-bromovaleric acid results in the preparation of corresponding products.

(b) Saponification of the ester 21.1 g (0.07 mol) of theophylline-(7)-butyric acid ether ester in 100 ml of ethanol are boiled under reflux with 6.17 g (0.11 mol) of potassium hydroxide for 15 minutes. The solution is evaporated in vacuo, the residue is dissolved in water and the resulting aqueous solution is acidified with 2 N hydrochloric acid until the precipitate no longer increases. The acid which has precipitated is filtered off and recrystallized from ethanol. 13.8 g (72.3 percent of the theoretically calculated amount) of theophylline-(7)-butyric acid of melting point 168° to 169° C. are thus obtained.

Corresponding acids are similarly produced from the propionic acid ethyl ester and from the valeric acid ethyl ester of theophylline-(7).

EXAMPLE 2

Preparation of theophylline-(7)-butyric acid N-[2-(4-hydroxyphenyl)ethyl]amide:

500 mg of theophylline-(7)-butyric acid are dissolved in 40 ml of anhydrous dimethylformamide, together with 326 mg of tyramine hydrochloride, 259 mg of 1-hydroxybenztriazole and 0.26 ml of triethylamine. 391 mg of dicyclohexylcarbodiimide dissolved in 10 ml of anhydrous dimethylformamide are added dropwise to this solution, while stirring. The mixture is stirred at 25° C. for 22 hours. The urea which has precipitated is filtered off, and the filtrate is evaporated in vacuo. The residue is taken up in methanol, to which 10 percent of chloroform has been added, and the mixture is applied to four PLC pre-coated silica gel 60 $F_{254}$ plates (Messrs. Merck, Darmstadt). After development with chloroform/methanol 9:1, the substance zones with an $R_f$ of 0.39 are scratched out, and the amide is eluted from the silica gel with methanol. The methanol solution is evaporated in vacuo, whereupon a colorless viscous oil remains which, on trituration with ether, crystallizes. 100 mg of theophylline-(7)-butyric acid N-[2-(4-hydroxyphenyl)ethyl]amide of melting point 158° to 162° C. are obtained in this manner. The amide is characterized in the mass spectrum by the molecular peak m/e=385.

Replacing theoplylline-(7)-butyric acid with an equivalent of theophylline-(7)-propionic or -valeric acid results in the similar preparation of the corresponding amides.

EXAMPLE 3

Theophylline labelled with $^{125}$iodine (theophilline tracer)

0.25 to 0.5 mCi of Na $^{125}$iodide (Amersham Buchler, Brunswick) and 10 µl of chloramine T solution (20 µg in 50 mmolar potassium phosphate buffer of pH 7.7 to 8.5) are added to 2 µg of theophylline-(7)-butyric acid N-[2-(4-hydroxyphenyl)ethyl]amide, 2 µg of theophylline-(7)-butyric acid N-(2-imidazol-4-ylethyl)amide or 2 µg of theophylline-(7)-butyryl-tyrosine or -tyrosine methyl ester or -tyrosine ethyl ester, dissolved in 20 µl of 50 mmolar potassium phosphate buffer of pH 7.7 to 8.5. After from 30 to 120 seconds, the reaction is stopped by adding 10 µl of sodium disulfite solution (50 82 g in 50 mmolar potassium phosphate buffer of pH 7.7 to 8.5) and 200 l of potassium iodide solution (2 mg in the identical phosphate buffer). Excess iodide is then separated off from the tracer by chromatography over a Sephadex-G-10 column (5×160 mm). Elution is effected with a phosphate buffer similar to that used for the reaction, except that 0.5 percent of bovine serum albumin (BSA) has also been added in this case. 0.5-ml fractions are collected; an aliquot of each fraction is counted to determine the activity. The fractions containing the iodine tracer are combined, and aliquots thereof are employed directly, after dilution, in the assay.

EXAMPLE 4

Fluorescence-labelled theophylline 0.88 g of theophylline-8-butyric acid methylester is heated at 190° C. with 1.3 g of 4-hydroxymethyl-7-methoxycoumarin and a few mg of 4-toluene sulfonic acid for two hours. The resulting melt is cooled down and heated to boiling with acetonitrile. The resulting crystal powder is filtered by suction and dried. In this manner 0.8 g of (7-methoxy-4-methylcourmarin)-theophylline-(8)-butyrate (56% of the theoretically calculated amount) of melting point 247° C. (decomposition) is obtained.

The starting materials are produced in the following way:

(a) Theophylline-8-butyric acid methylester 10 g of theophylline-8-butyric acid are suspended in 50 ml of methanol. For one hour HCl-gas is fed into the suspension. While further feeding HCl-gas into the suspension, heating for one hour under reflux is effected. The feed of HCl-gas is interrupted, and 13.5 ml of 2,2-dimethoxypropane are added to the suspension. Afterwards, for a further 20 minutes HCl-gas is fed into the suspension. After standing over night at room temperature, the suspension is brought to dryness in vacuo. The residue is dissolved in 300 ml of methylenechloride. After having extracted the methylenechloride phase twice with 100 ml of saturated aqueous soda solution and twice with 100 ml of water, it is dried over annealed sodium sulfate and brought to dryness in vacuo. The residue is recrystallized from methanol. In this way 5.15 g (48.4 percent of the theoretically-calculated amount) of the title compound of melting point 200° to 204° C. are obtained.

(b) 4-Hydroxy-7-methylcoumarin 10 g of 4-bromomethyl-7-methoxycoumarin [produced according to Secrist et al., *Biochem. Biophys. Res. Commun.*, 45, 1262 (1971)] are heated to boiling for 2.5 hours under reflux in 40 ml of glacial acetic acid together with 6 g of calcium acetate (free of water). The solution is brought to dryness in vacuo. The residue is heated to boiling in 50 ml of ethanol and 50 ml of concentrated hydrochloric acid for 1.5 hours under reflux. The volatile components are removed under reduced pressure. The residue is dissolved in chloroform. The resulting solution is made free of acids by extraction with diluted aqueous ammoniac and water and dried over annealed potassium carbonate. After removing the chloroform in vacuo, the residue is recrystallized from ethylacetate. In this manner 1.9 g (24.8 percent of the theoretically-calculated amount) of the title compound with a melting point of 179° to 182° C. are obtained.

(7-methoxy-4-methylcoumarin)-(theophylline-7-butyrate) is prepared in an analogous manner from equivalent amounts of corresponding reactants. The esterification of fatty acids with 4-hydroxy-7-methylcoumarin is described in Dunges, *Analyt. Chem.*, 49, 442 (1977) and Lam et al., *J. Chromatography*, 158, 207 (1978).

EXAMPLE 5

Preparation of the immunogen 1 mg of theophylline-(7)-butyric acid and 250 µg of N,N'-carbonyldiimidazole are added to 200 µl of dimethylformamide. After shaking the mixture for 5 minutes, 0.5 mg of BSA in 0.6 ml of water is added under a slight stream of nitrogen. The stream of nitrogen is turned off, and the closed vessel is shaken lightly at room temperature for from 5 to 12 hours. After this period, the resulting solution is dialyzed against doubly-distilled water and simultaneously concentrated, under a water-pump vacuum and while cooling in an ice-bath. Sartorius collodion tubes of the SM 13200 type are used for the dialysis. The antigen is then diluted with water to a concentration of 1 mg/ml.

EXAMPLE 6

Production of antibodies

100 µl, corresponding to about 0.1 mg of antigen, of the solution obtained according to Example 5 are emulsified with 300 µl of Freund's complete adjuvant, and rabbits (white Neuseeländer) are injected subcutaneously with the mixture over a period of several weeks to months. The animals are injected at several points, in each case with from about 50 to 100 µl. One week after the injection, blood is (in each case) taken from the animals from the ear vein, and the antisera [obtained by centrifuging, diluting with 0.1 M potassium phosphate buffer (pH 8.5), with the addition of 0.1 percent of gelatin and 0.04 percent of sodium azide, in the ratio 1:500] are employed in an immunoassay process for the determination of theophylline.

EXAMPLE 7

RIA process for the determination of theophylline

The following reagents and materials are used:
1. Small test tubes comprising small disposable culture tubes (12×75 mm)
2. A solution of $^{125}$iodine-labelled theophylline according to Example 3 in 100 molar potassium phosphate buffer of pH 8.5, with the addition of 0.1 percent of gelatin and 0.4 percent of sodium azide, which produces about 15,000 impulses/minute/0.1 ml.
3. Antiserum diluted in the ratio 1:2000 by the buffer described under 2.
4. Standard solutions of theophylline is phosphate buffer: 5, 25, 50, 100 and 250 mg/ml.
5. A suspension of active charcoal with dextran (Dextran T 70 and Norit active charcoal from Messrs. Pharmazie and Serva Feinbiochemica) in phosphate buffer, without the addition of gelatin.
6. 1, 2.5, 5 and 10 g/ml of theophylline are added to human control plasma, diluted in the ratio 1:50 to 1:200 with phosphate buffer (see 2), and the extent of recovery of theophylline is determined.
7. 200 µl of antibody dilution and 100 µl of theophylline tracer according to Example 3 are added to 20 µl of standard solution or diluted sample. After shaking the mixture for a short time, it is incubated at 4° C. for 1 hour and then, to separate off free and bonded theophylline, 1 ml of dextran/charcoal suspension is added, and the mixture is immediately shaken vigorously. After 10 minutes, it is centrifuged at 4° C. (15 minutes at about 2,000 g) and 1 ml of the supernatant liquor is removed and transferred to a small counting glass, and the radioactivity is determined in the customary manner.

0.1 to 1 ng of theophylline or even less is determined in a small tube in this manner. If a sample of 20 µl (as serum dilution or standard dilution) is used, the sensitivity limit is 35 ng/ml (95 percent confidence limit).

If the concentrations employed are inserted on the abscissa of a log-logit graph paper and the factor $$\frac{B}{Bo} \times 100 \left( \frac{\text{bonding sample}}{\text{bonding antibody}} \times 100 \right)$$

is inserted as the ordinate, the standard curve is thus linearized, and the concentration of unknown samples is read directly in the customary manner.

The invention and its advantages are readily understood from the preceding description. Various changes may be made in the IGC of the antigen in the antiserum, in the antibody, in components of the reagent, in the theophylline/antibody complex, in the labelled theophylline, in the process for producing antiserum, in the employed host animal, in the RIA method, in the EIA method and in the FIA method without departing from the spirit or scope of the invention or sacrificing its material advantages. The precursors, the intermediates, the products and the processes hereinbefore described are merely illustrative of preferred embodiments of the invention.

I claim:

1. An antigen in the structure of which a haptene of the formula $$T-(CH_2)_n-COOH$$

wherein
T is theophylline-(7) and
n is an integer from 2 to 4, inclusive,
is covalently bonded via the carbonyl group to an immunogenic carrier.

2. An antigen according to claim 1 wherein the immunogenic carrier is a protein.

3. An antigen according to claim 2 wherein the protein is a mammalian serum protein selected from the group consisting of human γ-globulin, human serum albumin, hare serum albumin, bovine γ-globulin and bovine serum albumin.

4. An antigen according to claim 1 wherein the immunogenic carrier is a polypeptide.

5. An antigen according to claim 4 wherein the polypeptide is a synthetic polypeptide selected from the group consisting of a polymer of lysine and a polymer of glutamic acid.

6. An antigen according to claim 1 wherein n is 3.

7. An antigen according to claim 1 wherein the immunogenic carrier is bovine serum albumin.

8. Antigen-stimulated animal-blood antiserum for which the antigen is an antigen according to claim 1.

9. A reagent for theophylline determination comprising an admixture of labelled theophylline and antiserum according to claim 8.

10. A theophylline/antibody complex wherein the antibody is that of antiserum according to claim 8.

11. A complex according to claim 10 wherein the theophylline is labelled theophylline.

12. A theophylline/antibody complex according to claim 11 wherein the labelled theophylline is radioactively labelled.

13. A complex according to claim 12 wherein the radioactively-labelled theophylline is that which is labelled with a radioisotope selected from the group consisting of tritium, carbon 14, iodine 125 and iodine 131.

14. A complex according to claim 12 wherein the radioactively-labelled theophylline is theophylline-(7)- butyric acid N-[2-(4-hydroxyphenyl)ethyl]amide iodinated with $^{125}$iodine.

15. A complex according to claim 12 wherein the radioactively-labelled thoephylline is theophylline-(7)-butyric acid N-(2-imidazol-4-ylethyl)amide iodinated with $^{125}$iodine.

16. A complex according to claim 12 wherein the radioactively-labelled theophylline is theophylline-(7)-butyryl-tyrosine, -tyrosine methylester or -tyrosine ethyl ester iodinated with $^{125}$iodine.

17. A theophylline/antibody complex according to claim 11 wherein the labelled theophylline is enzyme labelled.

18. A complex according to claim 17 wherein the enzyme-labelled theophylline is that which is labelled with glucose-6-phosphate-dehydrogenase.

19. A theophylline/antibody complex according to claim 11 wherein the labelled theophylline is fluorescent labelled.

20. A complex according to claim 19 wherein the fluorescent-labelled theophylline is that which is labelled with 7-methoxy-4-methylcoumarin.

21. A complex according to claim 19 wherein the fluorescent-labelled theophylline is that which is labelled with fluorescein.

22. A theophylline/antibody complex according to claim 10 wherein the theophylline comprises both labelled and unlabelled form.

23. An antibody of antiserum according to claim 8.

24. In a process of producing antiserum useful for theophylline determination which comprises injecting a host animal with an antigen the improvement wherein the antigen is an antigen according to claim 1.

25. A theophylline determination method which comprises forming a theophylline/antibody complex by admixing a sample having an unknown theophylline content with a known amount of labelled theophylline and an antibody according to claim 23 and detecting the amount of labelled theophylline.

26. A method according to claim 25 which further comprises measuring the degree of binding of the labelled theophylline and comparing same against a standard curve obtained by adding known amounts of theophylline to a mixture of labelled theophylline and the antibody.

27. A method according to claim 26 wherein the labelled theophylline is radio-labelled theophylline.

28. A method according to claim 26 wherein the labelled theophylline is enzyme-labelled theophylline.

29. A method according to claim 26 wherein the labelled theophylline is fluorescence-labelled theophylline.

30. In an immunoassay reagent composition in which antiserum is in admixture with a labelled compound, the improvement wherein the antiserum is mammal-blood antiserum according to claim 8 and the labelled compound is one which forms a complex with antibodies of said antiserum.

31. An immunoassay reagent composition according to claim 30 for theophylline determination and in which the labelled compound is labelled theophylline or a labelled derivative of theophylline.

32. A reagent according to claim 31 wherein the labelled compound is radioactively labelled.

33. A reagent according to claim 32 wherein the radioactively-labelled compound is theophylline-(7)-butyric acid N-[2-(4-hydroxyphenyl)ethyl]amide iodinated with $^{125}$iodine.

34. A reagent according to claim 32 wherein the radioactively-labelled compound is theophylline-(7)-butyric acid N-(2-imidazol-4-ylethyl)amide iodinated with $^{125}$iodine.

35. A reagent according to claim 32 wherein the radioactively-labelled compound is theophylline-(7)-butyryl-tyrosin, -tyrosin methylester or -tyrosin ethyl ester iodinated with $^{125}$iodine.

36. A reagent according to claim 31 wherein the labelled compound is enzyme labelled.

37. A reagent according to claim 36 wherein the enzyme-labelled compound is labelled with glucose-6-phosphate-dehydrogenase.

38. A reagent according to claim 31 wherein the labelled compound is fluorescent labelled.

39. A reagent according to claim 38 wherein the fluorescent-labelled compound is labelled with 7-methoxy-4-methylcoumarin.

40. A reagent according to claim 38 wherein the fluorescent-labelled compound is labelled with fluorescein.

* * * * *